US010823798B2

(12) United States Patent
Van Den Brink (10) Patent No.: US 10,823,798 B2
(45) Date of Patent: Nov. 3, 2020

(54) VIRTUAL CT IMAGES FROM MAGNETIC RESONANCE IMAGES

(71) Applicant: KONINKLIJKE PHILIPS N.V., Eindhoven (NL)

(72) Inventor: Johan Samuel Van Den Brink, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 54 days.

(21) Appl. No.: 15/768,056

(22) PCT Filed: Oct. 21, 2016

(86) PCT No.: PCT/EP2016/075328
§ 371 (c)(1),
(2) Date: Apr. 13, 2018

(87) PCT Pub. No.: WO2017/072034
PCT Pub. Date: May 4, 2017

(65) Prior Publication Data
US 2018/0321345 A1 Nov. 8, 2018

(30) Foreign Application Priority Data

Oct. 27, 2015 (EP) .................................... 15191663

(51) Int. Cl.
*G01R 33/48* (2006.01)
*G01R 33/56* (2006.01)
(Continued)

(52) U.S. Cl.
CPC ....... *G01R 33/4812* (2013.01); *G01R 33/563* (2013.01); *G01R 33/5608* (2013.01);
(Continued)

(58) Field of Classification Search
CPC .............. G01R 33/4812; G01R 33/563; G01R 33/5608; G06T 11/003; G06T 7/0012;
(Continued)

(56) References Cited

U.S. PATENT DOCUMENTS

| | | | |
|---|---|---|---|
| 2004/0101088 A1* | 5/2004 | Sabol | A61B 6/481 378/4 |
| 2006/0098856 A1* | 5/2006 | Botterweck | A61B 6/032 382/131 |

(Continued)

FOREIGN PATENT DOCUMENTS

| | | |
|---|---|---|
| WO | 2014161766 A1 | 10/2014 |
| WO | 2015081079 A1 | 6/2015 |
| WO | 2015103184 A1 | 7/2015 |

OTHER PUBLICATIONS

Hsu et al "Investigation of a Method for Generating Synthetic CT Models From MRI Scans of the Head and Neck for Radiation Therapy" Physics in Med. and Bio. 58.23 (2013) Oct. 2015.
(Continued)

*Primary Examiner* — Susan S Lee
(74) *Attorney, Agent, or Firm* — Sherry Austin (57) ABSTRACT

A medical imaging system comprising: a memory and a processor configured by machine executable instructions that cause the processor to: receive multiple magnetic resonance images, the multiple magnetic resonance images comprising voxels; calculate an image segmentation for each of the multiple magnetic resonance images, the image segmentation dividing each of the multiple magnetic resonance images into regions; assign a tissue classification to each of the regions using a magnetic resonance imaging tissue classifier; calculate a Hounsfield unit map for each of the multiple magnetic resonance images by assigning a Hounsfield unit value to each of the voxels according to the tissue classification, the Hounsfield mapping comprising a
(Continued)

mapping between the tissue classification to Hounsfield units; and calculate a virtual CT image for each of the multiple magnetic resonance images using the Hounsfield unit mapping.

16 Claims, 5 Drawing Sheets (51) Int. Cl.
*G01R 33/563* (2006.01)
*G06T 7/00* (2017.01)
*G06T 11/00* (2006.01)
*A61B 6/00* (2006.01)
*A61B 6/03* (2006.01)

(52) U.S. Cl.
CPC .......... *G06T 7/0012* (2013.01); *G06T 11/003* (2013.01); *A61B 6/032* (2013.01); *A61B 6/481* (2013.01); *A61B 6/5217* (2013.01); *A61B 6/5223* (2013.01); *A61B 6/5247* (2013.01); *A61B 6/5294* (2013.01)

(58) Field of Classification Search
CPC ....... A61B 6/5294; A61B 6/481; A61B 6/032; A61B 6/5247; A61B 6/5217; A61B 6/5223
See application file for complete search history.

(56) References Cited

U.S. PATENT DOCUMENTS

2011/0286649 A1   11/2011   Reisman et al.
2013/0190602 A1    7/2013   Liao et al.
2013/0266198 A1   10/2013   Pereira et al.

OTHER PUBLICATIONS

Cocosco et al "A Fully Automatic and Robust Brain MRI Tissue Classification Method" Medical Image Analysis 7 (2003) p. 513-527.

M. Hofmann et al: "MRI-Based Attenuation Correction for Whole-Body PET/MRI: Quantitative Evaluation of Segmentation-and Atlas-Based Methods",The Journal DP Nuclear Medicine, vol. 52, No. 9, Sep. 1, 2011 (Sep. 1, 2011), pp. 1392-1399.

Thomas Beyer et al: "MR-based attenuation correction for torso-PET/MR imaging: pitfalls in mapping MR to CT data", European Journal of Nuclear Medicine and Molecular Imaging, Springer, Berlin, DE, vol. 35, No. 6, Feb. 19, 2008 (Feb. 19, 2008), pp. 1142-1146.

Christopher M Rank et al: "MRI-based treatment plan simulation and adaptation for ion radiotherapy using a classification-based approach",Radiation Oncology, Biomed Central Ltd, LO,vol. 8,No. 1, Mar. 6, 2013.

* cited by examiner

VIRTUAL CT IMAGES FROM MAGNETIC RESONANCE IMAGES

CROSS REFERENCE TO RELATED APPLICATIONS

This application is a U.S. national phase application of International Application No. PCT/EP2016/075328, filed on Oct. 21, 2016, which claims the benefit of EP Application Serial No. 15191663.2 filed on Oct. 27, 2015 and is incorporated herein by reference.

TECHNICAL FIELD OF THE INVENTION

The invention relates to magnetic resonance imaging, in particular to the calculation of virtual CT images from a multiple magnetic resonance images.

BACKGROUND OF THE INVENTION

Synthetic or virtual Computed Tomography (CT) images are simulated CT images calculated using data from one or more other medical imaging modalities. The journal article Hsu, Shu-Hui et al. "Investigation of a Method for Generating Synthetic CT Models from MRI Scans of the Head and Neck for Radiation Therapy." Physics in medicine and biology 58.23 (2013): 10.1088/0031-9155/58/23/8419. PMC. Web. 14 Oct. 2015 describes one method of generating virtual CT images.

The journal article Cocosco et. al., "A fully automatic and robust brain MRI tissue classification method," Medical Image Analysis 7 (2003) 513-527 describes a method of identifying different tissues types of brain tissues using an Magnetic Resonance Image (MRI).

The paper '*MRI-based attenuation correction for whole-body PET/MRI: quantitative evaluation of segmentation and atlas based methods*' by M. Hoffmann et al. in The Journal of Nuclear Medicine 52(2011)1392 (D1) concerns MR image segmentation and tissue class discrimination to create pseudo-CT images that serve for attenuation correction in (MR image guided) PET imaging. A dual echo sequence and a 2-point Dixon method are used to acquire a series of MR images. This series of MR images forms the basis of a five-class segmentation for the contrast type of the dual echo sequence.
Document D1 concerns the problem of constructing an adequate attenuation correction from MR image data.

SUMMARY OF THE INVENTION

The invention provides for a medical imaging system, computer program product and a method in the independent claims. Embodiments are given in the dependent claims.

As will be appreciated by one skilled in the art, aspects of the present invention may be embodied as an apparatus, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer executable code embodied thereon.

Any combination of one or more computer readable medium(s) may be utilized. The computer readable medium may be a computer readable signal medium or a computer readable storage medium. A 'computer-readable storage medium' as used herein encompasses any tangible storage medium which may store instructions which are executable by a processor of a computing device. The computer-readable storage medium may be referred to as a computer-readable non-transitory storage medium. The computer-readable storage medium may also be referred to as a tangible computer readable medium. In some embodiments, a computer-readable storage medium may also be able to store data which is able to be accessed by the processor of the computing device. Examples of computer-readable storage media include, but are not limited to: a floppy disk, a magnetic hard disk drive, a solid state hard disk, flash memory, a USB thumb drive, Random Access Memory (RAM), Read Only Memory (ROM), an optical disk, a magneto-optical disk, and the register file of the processor. Examples of optical disks include Compact Disks (CD) and Digital Versatile Disks (DVD), for example CD-ROM, CD-RW, CD-R, DVD-ROM, DVD-RW, or DVD-R disks. The term computer readable-storage medium also refers to various types of recording media capable of being accessed by the computer device via a network or communication link. For example a data may be retrieved over a modem, over the internet, or over a local area network. Computer executable code embodied on a computer readable medium may be transmitted using any appropriate medium, including but not limited to wireless, wire line, optical fiber cable, RF, etc., or any suitable combination of the foregoing.

A computer readable signal medium may include a propagated data signal with computer executable code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

'Computer memory' or 'memory' is an example of a computer-readable storage medium. Computer memory is any memory which is directly accessible to a processor. 'Computer storage' or 'storage' is a further example of a computer-readable storage medium. Computer storage is any non-volatile computer-readable storage medium. In some embodiments computer storage may also be computer memory or vice versa.

A 'processor' as used herein encompasses an electronic component which is able to execute a program or machine executable instruction or computer executable code. References to the computing device comprising "a processor" should be interpreted as possibly containing more than one processor or processing core. The processor may for instance be a multi-core processor. A processor may also refer to a collection of processors within a single computer system or distributed amongst multiple computer systems. The term computing device should also be interpreted to possibly refer to a collection or network of computing devices each comprising a processor or processors. The computer executable code may be executed by multiple processors that may be within the same computing device or which may even be distributed across multiple computing devices.

Computer executable code may comprise machine executable instructions or a program which causes a processor to perform an aspect of the present invention. Computer executable code for carrying out operations for aspects of the present invention may be written in any combination of one or more programming languages, including an object oriented programming language such as Java, Smalltalk, C++ or the like and conventional procedural programming languages, such as the "C" programming language or similar programming languages and compiled into machine executable instructions. In some instances the computer executable code may be in the form of a high level language or in a pre-compiled form and be used in conjunction with an interpreter which generates the machine executable instructions on the fly.

The computer executable code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described with reference to flowchart illustrations and/or block diagrams of methods, apparatus (systems) and computer program products according to embodiments of the invention. It is understood that each block or a portion of the blocks of the flowchart, illustrations, and/or block diagrams, can be implemented by computer program instructions in form of computer executable code when applicable. It is further under stood that, when not mutually exclusive, combinations of blocks in different flowcharts, illustrations, and/or block diagrams may be combined. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

A 'user interface' as used herein is an interface which allows a user or operator to interact with a computer or computer system. A 'user interface' may also be referred to as a 'human interface device.' A user interface may provide information or data to the operator and/or receive information or data from the operator. A user interface may enable input from an operator to be received by the computer and may provide output to the user from the computer. In other words, the user interface may allow an operator to control or manipulate a computer and the interface may allow the computer indicate the effects of the operator's control or manipulation. The display of data or information on a display or a graphical user interface is an example of providing information to an operator. The receiving of data through a keyboard, mouse, trackball, touchpad, pointing stick, graphics tablet, joystick, gamepad, webcam, headset, pedals, wired glove, remote control, and accelerometer are all examples of user interface components which enable the receiving of information or data from an operator.

A 'hardware interface' as used herein encompasses an interface which enables the processor of a computer system to interact with and/or control an external computing device and/or apparatus. A hardware interface may allow a processor to send control signals or instructions to an external computing device and/or apparatus. A hardware interface may also enable a processor to exchange data with an external computing device and/or apparatus. Examples of a hardware interface include, but are not limited to: a universal serial bus, IEEE 1394 port, parallel port, IEEE 1284 port, serial port, RS-232 port, IEEE-488 port, Bluetooth connection, Wireless local area network connection, TCP/IP connection, Ethernet connection, control voltage interface, MIDI interface, analog input interface, and digital input interface.

A 'display' or 'display device' as used herein encompasses an output device or a user interface adapted for displaying images or data. A display may output visual, audio, and or tactile data. Examples of a display include, but are not limited to: a computer monitor, a television screen, a touch screen, tactile electronic display, Braille screen, Cathode ray tube (CRT), Storage tube, Bi-stable display, Electronic paper, Vector display, Flat panel display, Vacuum fluorescent display (VF), Light-emitting diode (LED) displays, Electroluminescent display (ELD), Plasma display panels (PDP), Liquid crystal display (LCD), Organic light-emitting diode displays (OLED), a projector, and Head-mounted display.

Magnetic Resonance (MR) data is defined herein as being the recorded measurements of radio frequency signals emitted by atomic spins using the antenna of a Magnetic resonance apparatus during a magnetic resonance imaging scan. Magnetic resonance data is an example of medical image data. A Magnetic Resonance Imaging (MRI) image is defined herein as being the reconstructed two or three dimensional visualization of anatomic data contained within the magnetic resonance imaging data. This visualization can be performed using a computer.

In one aspect the invention provides for a medical imaging system. The medical imaging system comprises a memory for storing machine-executable instructions. The medical imaging system further comprises a processor for controlling the medical system. The machine-executable instructions are executable by the processor. Execution of the machine-executable instructions causes the processor to receive multiple magnetic resonance images. The multiple magnetic resonance images may for example be of a subject and taken in sequence or in series. The multiple magnetic resonance images may be of the same portion of anatomy of a subject. Each of the multiple magnetic resonance images comprise voxels. The multiple magnetic resonance images may be received via a network or other computer storage medium. In other examples the multiple magnetic resonance images are acquired by the medical imaging system.

Execution of the machine-executable instructions further cause the processor to calculate an image segmentation for each of the multiple magnetic resonance images. The image segmentation divides each of the magnetic resonance images into regions. Execution of the machine-executable instructions further cause the processor to assign a tissue classification to each of the regions using a magnetic resonance imaging tissue classifier. The image segmentation may for instance be performed using standard techniques such as image processing for looking at abrupt changes in the values of voxels or for example a deformable model or other anatomical model may be used to determine the image segmentation.

Likewise the magnetic resonance imaging tissue classifier may use standard techniques. For example an anatomical model may be used at least partially in some examples. In other examples the magnetic resonance imaging tissue classifier may work by determining an average or a mean value of the voxels within a particular region. These may be normalized or scaled and then compared to a standard to identify a tissue type and assign a tissue classification.

Execution of the machine-executable instructions further cause the processor to calculate a Hounsfield unit map for each of the multiple magnetic resonance images by assigning a Hounsfield unit value to each of the voxels according to the tissue classification. The Hounsfield mapping comprises a mapping between the tissue classification to Hounsfield units. Execution of the machine-executable instructions further cause the processor to calculate a virtual CT or computer tomography image for each of the multiple magnetic resonance images using the Hounsfield unit mapping. This embodiment may have the benefit that it provides for an improved way of making virtual CT images for groups of magnetic resonance images.

In another embodiment the magnetic resonance imaging tissue classification may assign one of a finite number of tissue types to each region.

In particular, diagnostic MR images having various contrast types and high-spatial resolution and signal-to-noise level for adequate diagnostic image quality are used as a basis for the virtual CT images. These virtual CT images corresponding to the diagnostic quality MR images may be used to support a physician to interpret the MR images.

In another embodiment the medical system further comprises a magnetic resonance imaging system for acquiring a multiple series of magnetic resonance data from a subject. In some examples the multiple series may be a time series. The memory further stores pulse sequence commands. The pulse sequence commands may contain instructions or controls which the processor uses to control the magnetic resonance imaging system to acquire the multiple series of magnetic resonance data according to a magnetic resonance imaging protocol. Execution of the machine-executable instructions further cause the processor to acquire the multiple series of magnetic resonance data by controlling the magnetic resonance imaging system with the pulse sequence commands. Execution of the machine-executable instructions further cause the processor to reconstruct the multiple series of magnetic resonance data into the multiple magnetic resonance image. This embodiment may have the benefit of providing for an improved method of generating virtual CT images for a multiple series or time series of magnetic resonance images.

In another embodiment, the pulse sequence commands specify a first echo time greater than 100 μs. This may have the benefit of enabling the calculation of virtual CT images without the so called UTE or ultra short echo time pulse sequences. Another potential benefit is that using a longer echo time may makes the MR sequence more sensitive to pathology and supports more accurate tissue classification.

In another embodiment the pulse sequence commands cause the magnetic resonance imaging system to acquire the multiple series of magnetic resonance data according to an arterial spin labeling magnetic resonance imaging protocol. This embodiment may be useful because it provides a means of converting a standard arterial spin labeled magnetic resonance image into a virtual or pseudo CT image. This may enable physicians or other personnel who are used to examining CT images to be able to more easily interpret the arterial spin labeled magnetic resonance image.

In another embodiment the pulse sequence commands comprise commands for any one of the following: a gradient echo pulse sequence, a TSE sequence, a spin echo, a Dixon pulse sequence, and combinations thereof. In other embodiments pulse sequence commands may be used for labeling or marking diffusion within the subject. In another example the pulse sequence commands may cause sampling in the k-space to be performed in a Cartesian, radial or spiral pattern.

In another embodiment the pulse sequence commands cause the magnetic resonance data to be acquired using an EPI pulse sequence.

In another embodiment the pulse sequence commands cause the processor to acquire magnetic resonance data by varying any one of the following: the flip angle, the TE or echo time, the TR or repetition time, and combinations thereof. This may have several different benefits. In some cases modifying the flip angle, TE and/or TR may have an effect on the contrast or brightness of the voxels and may enable different features to be seen within the magnetic resonance images.

In other examples this variation of the flip angle, TE, and/or TR could be used for a so called MR fingerprinting magnetic resonance imaging protocol. In magnetic resonance fingerprinting pulse sequence commands cause the data to be acquired using a predetermined but pseudo random variation of flip angle, TE, TR and combinations. A dictionary can then be calculated for each of a set number of tissue types. The dictionary contains a number of signals for each particular tissue type. The magnetic resonance fingerprinting then acquires the magnetic resonance data using the pulse sequence commands, and the acquired magnetic resonance data is compared to the magnetic resonance fingerprinting dictionary. The magnetic resonance signal can then be decomposed voxel-by-voxel and compared to the dictionary and the fraction of each voxel which contains the various tissue types can then be mapped. This may have the benefit of being able to perform the method more rapidly, and also in some cases to be able to produce a more accurate tissue classification for each of the regions of the magnetic resonance imaging tissue classifier. In this embodiment the magnetic resonance imaging tissue classifier is the magnetic resonance fingerprinting dictionary.

In another embodiment the medical imaging system further comprises a display. Execution of the machine-executable instructions further cause the processor to display the virtual CT image for each of the multiple magnetic resonance images. The display of the various virtual CT images may in some examples have them all displayed at the same time. In other examples they may be displayed sequentially or in a predetermined order.

In another embodiment the virtual CT image is displayed next to a corresponding image. The corresponding image is selected from the multiple magnetic resonance images. This may have the benefit of providing a virtual CT image which may be useful in a physician or other person understanding the contents of the magnetic resonance image.

In another embodiment the finite tissue types comprise any one of the following: water, fat, hepatocellular carcinoma cells, carcinoma cells, cyst cells, arteries, veins, metastasis cells, bone tissue, blood, epithelial cells, muscle tissue, interstitial cells, nerve tissue, connective tissue, cartilage, and combinations thereof.

In another embodiment the multiple magnetic resonance images comprise at least one pre-contrast image or a late post-contrast image.

In another embodiment the multiple magnetic resonance images further comprise at least an arterial phase image.

In another embodiment the multiple magnetic resonance images comprise at least one post-venous phase image.

In another embodiment the multiple magnetic resonance images comprise at least one late enhancement image.

In another embodiment the magnetic resonance imaging tissue classifier assigns a tissue classification to each of the regions at least partially using an anatomical model. For example a deformable model or other anatomical model could be used to either completely classify or aid in classifying the tissue types.

In another embodiment the anatomical model comprises any one of the following: a prostrate model, a liver model, and combinations thereof.

In another embodiment the magnetic resonance imaging tissue classifier assigns a tissue classification to each of the regions at least partially by: computing a representative voxel value of each of the regions, normalizing the representative voxel value for each of the regions, and assigning the tissue classification to each of the regions by matching the normalized representative voxel with a predetermined range for the tissue classification. When magnetic resonance images are acquired the absolute intensity of the voxels may not be calibrated.

However, the relative intensity of the voxels for particular tissue types is determined. The representative voxel value may be a statistical measure such as a mean or average for the voxel values within a particular region. These can then be normalized or for example scaled against the region with the largest value so that the voxels are within certain standard ranges. The normalized representative voxel value can then be compared against a table or mapping which maps intensities of a particular range for a particular tissue classification. For example a vector could be constructed for all of the various regions and then this vector could be compared against a standard vector and the tissue types are then assigned to the value which most closely matches in a reference vector.

In another embodiment execution of the machine-executable instructions further cause the processor to assign LIRADS example images based on pre-identified shapes and image intensity variations to identify tissue types in the virtual CT image for each of the multiple magnetic resonance images. This for instance may be useful in providing information which may be useful in diagnosing or describing abnormalities in the magnetic resonance images.

In another embodiment execution of the machine executable instructions further cause the processor to acquire the multiple series of magnetic resonance data within a duration of one hour. For example the magnetic resonance data may be acquired after a contrast agent has been injected into the subject.

In another embodiment the virtual CT image for each of the multiple magnetic resonance images is stored in an image database.

In another aspect the invention provides for a computer program product comprising machine-executable instructions for execution by a processor controlling the medical imaging system. Execution of the machine-executable instructions causes the processor to receive multiple magnetic resonance images. Each of the multiple magnetic resonance images comprises voxels. Execution of the machine-executable instructions further causes the processor to calculate an image segmentation for each of the multiple magnetic resonance images. The image segmentation divides each of the multiple magnetic resonance images into regions. Execution of the machine-executable instructions further cause the processor to assign a tissue classification to each of the regions using a magnetic resonance imaging tissue classifier. Execution of the machine-executable instructions further cause the processor to calculate a Hounsfield unit map for each of the multiple magnetic resonance images by assigning a Hounsfield unit value to each of the voxels according to the tissue classification. The Hounsfield mapping comprises a mapping between the tissue classification to the Hounsfield units. Execution of the machine-executable instructions further cause the processor to calculate a virtual CT image for each of the multiple magnetic resonance images using the Hounsfield unit mapping.

In another aspect the invention provides for a method of operating a medical imaging system. The method comprises receiving multiple magnetic resonance images. Each of the multiple magnetic resonance images comprises voxels. The method further comprises calculating an image segmentation for each of the multiple magnetic resonance images. The image segmentation divides each of the multiple magnetic resonance images into regions. The method further comprises assigning a tissue classification to each of the regions using a magnetic resonance imaging tissue classifier. The method further comprises calculating a Hounsfield unit map for each of the multiple magnetic resonance images by assigning a Hounsfield unit value to each of the voxels according to the tissue classification. The Hounsfield mapping comprises a mapping between the tissue classification to the Hounsfield units. The method further comprises calculating a virtual CT image for each of the multiple magnetic resonance images using the Hounsfield unit mapping.

In another aspect the invention provides for a medical imaging system. The magnetic resonance imaging system comprises a memory for storing machine-executable instructions. The medical imaging system further comprises a processor for controlling the medical imaging system. Execution of the machine-executable instructions cause the processor to receive multiple magnetic resonance images. Each of the multiple magnetic resonance images comprises voxels. Execution of the machine-executable instructions further cause the processor to calculate an image segmentation for each of the multiple magnetic resonance images. The image segmentation divides each of the multiple magnetic resonance images into regions. Execution of the machine-executable instructions further cause the processor to assign a tissue classification to each of the regions using the magnetic resonance imaging tissue classifier. Execution of the machine-executable instructions further cause the processor to calculate a Hounsfield unit map from the magnetic resonance image by assigning a Hounsfield unit value to each of the voxels according to the tissue classification. The Hounsfield mapping comprises a mapping between the tissue classification to Hounsfield units. Execution of the machine-executable instructions further cause the processor to calculate a virtual CT image for each of the multiple magnetic resonance images using the Hounsfield unit mapping.

It is understood that one or more of the aforementioned embodiments of the invention may be combined as long as the combined embodiments are not mutually exclusive.

BRIEF DESCRIPTION OF THE DRAWINGS

In the following preferred embodiments of the invention will be described, by way of example only, and with reference to the drawings in which.

DETAILED DESCRIPTION OF THE EMBODIMENTS

Like numbered elements in these figures are either equivalent elements or perform the same function. Elements which have been discussed previously will not necessarily be discussed in later figures if the function is equivalent.

Figure 1:
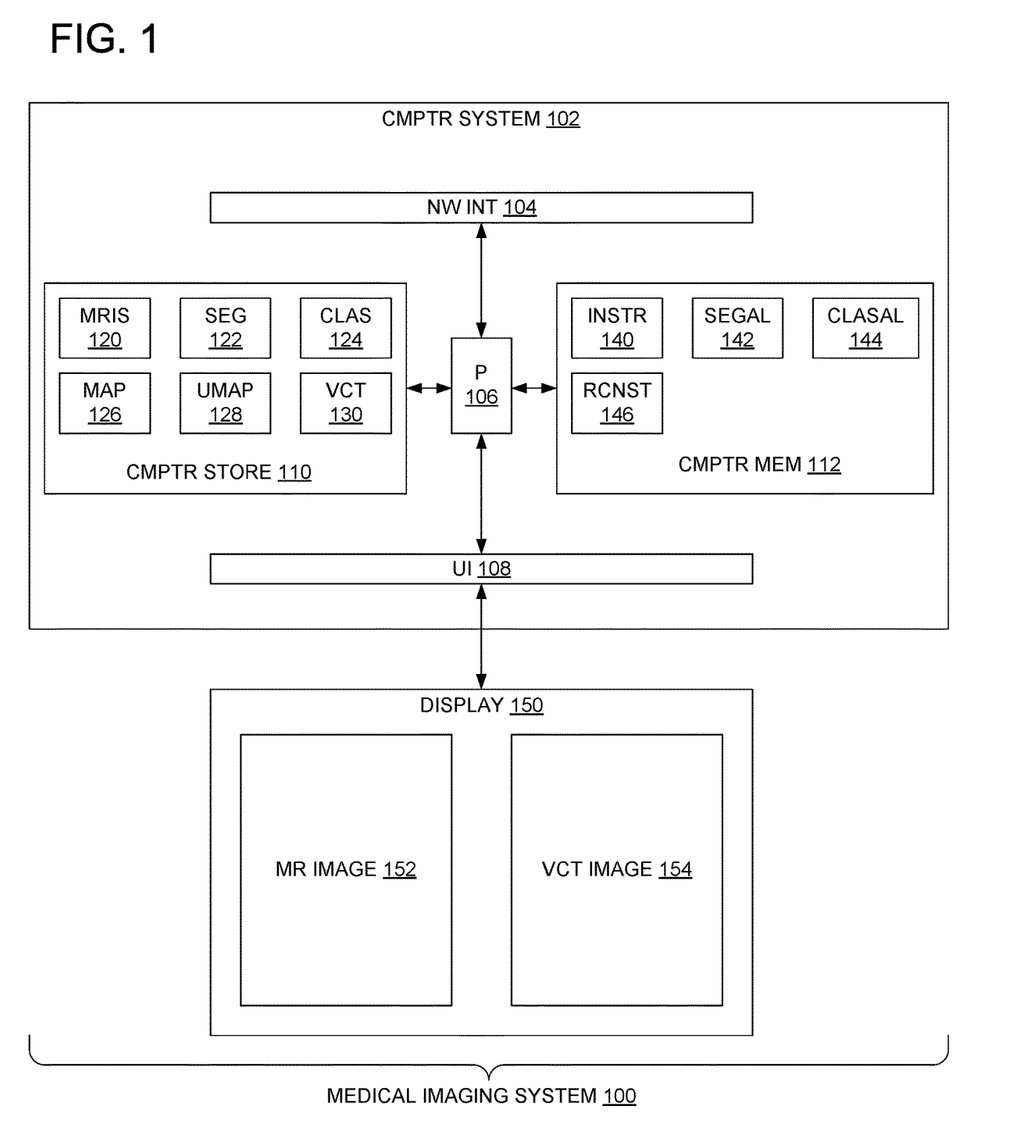
FIG. 1 illustrates an example of a medical imaging system.

FIG. 1 shows an example of a medical imaging system 100. The medical imaging system 100 is shown as comprising a computer system 102. The computer system 102 may for instance have a hardware 104 or a network interface. The computer system is further shown as containing a processor 106 that is connected to the hardware or network interface 104, a user interface 108, computer storage 110, and computer memory 112.

The computer storage 110 is shown as containing multiple magnetic resonance images. The computer storage 110 is further shown as containing a segmentation of the multiple magnetic resonance images 120. The computer storage 110 is further shown as containing a tissue classification 124 that was derived from the segmentation of the multiple magnetic resonance images 122. The computer storage 110 is further shown as containing a mapping between the tissue classification and the Hounsfield units 126. The computer storage 110 is further shown as containing a Hounsfield unit map 128 that was constructed from the tissue classifications 124 and the mapping between the tissue classifications and the Hounsfield units. The computer storage 110 is further shown as containing a virtual CT image that was reconstructed from the Hounsfield unit maps 128 of the multiple magnetic resonance images 120. The computer memory 112 is shown as containing machine-executable instructions 140 that enable the processor 106 to control the operation and function of the medical imaging system 100. The computer storage 112 is further shown as containing a segmentation algorithm 142 which contains executable code which enables the processor 106 to segment the multiple magnetic resonance images 120 into the segmentations 122.

The computer memory 112 is further shown as containing a magnetic resonance imaging system tissue classifier 144 which enables the tissue classification 124 to be derived from the segmentations 122. The computer storage 112 is further shown as containing an image processing module 146 which contains executable code which enables the processor 106 to perform such things as creating the mappings 126 or reconstruct the virtual CT image 130 from a Hounsfield unit map 128. In the case that the medical imaging system 100 also comprises a magnetic resonance imaging system the imaging processing module 146 may also contain code which enables the processor 106 to reconstruct magnetic resonance data into magnetic resonance images. The contents of the computer storage 110 and the computer memory 112 may be combined, they may be duplicated or exchanged with each other.

The medical imaging system 100 is further shown as comprising a display 150. The display 150 displays a magnetic resonance image 152 and next to it a virtual CT image 154. The virtual CT image 154 was derived from the magnetic resonance image 152. Displaying them next to each other may be advantageous because it may enable a physician or other person who is accustomed to seeing CT images to better interpret the magnetic resonance image 152.

Figure 2:
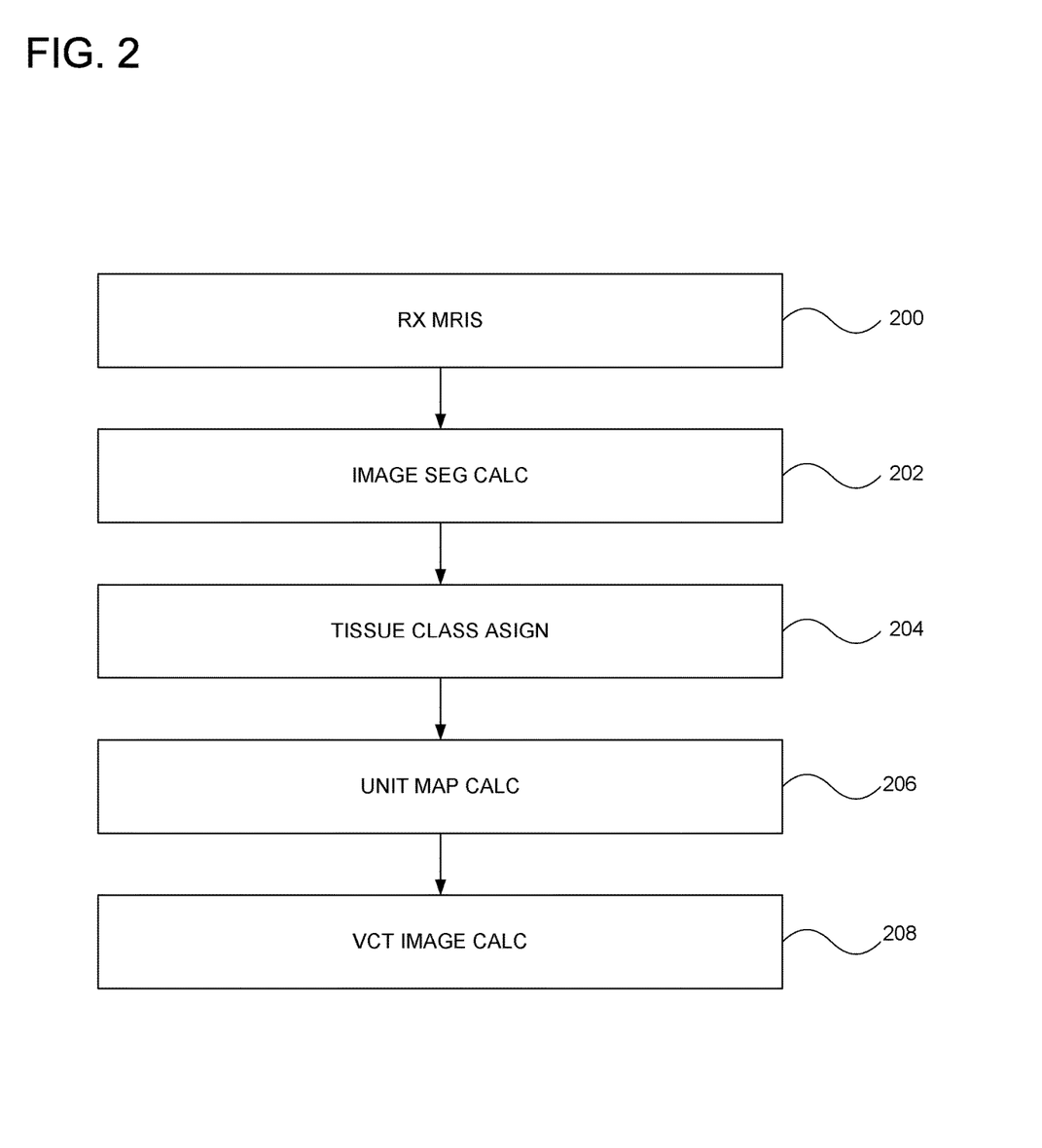
FIG. 2 shows a flow chart that illustrates a method of operating the medical imaging system of FIG. 1.

FIG. 2 shows a flowchart which illustrates an example of a method of operating the medical imaging system 100 of FIG. 1. First in step 200 the multiple magnetic resonance images 120 are received. These for instance could be received by acquiring and reconstructing magnetic resonance images, they could be received via a network interface, or they could be brought by a computer storage medium to the computer system 102. Next in step 202 an image segmentation 122 is calculated for each of the multiple magnetic resonance images 120. Next in step 204 tissue classification 124 is assigned to each of the regions using a magnetic resonance imaging tissue classifier algorithm 144. Next in step 206 the Hounsfield unit map 128 is calculated for each of the multiple magnetic resonance images 120 by assigning a Hounsfield unit value to each of the voxels according to the tissue classification 124.

As an alternative, a single Hounsfield unit map 128 is calculated from a combination of data from the multiple magnetic resonance images. For example the multiple magnetic resonance images could be averaged before segmentation. In another example the segmentation data from each of the multiple magnetic resonance images is combined to create a combined image segmentation. The combined image segmentation is then assigned tissue classifications, which are then used to calculate a Hounsfield unit map.

Finally in step 208 a virtual CT image 130 is calculated for each of the magnetic resonance images 120 using the Hounsfield unit map 128.

Figure 3:
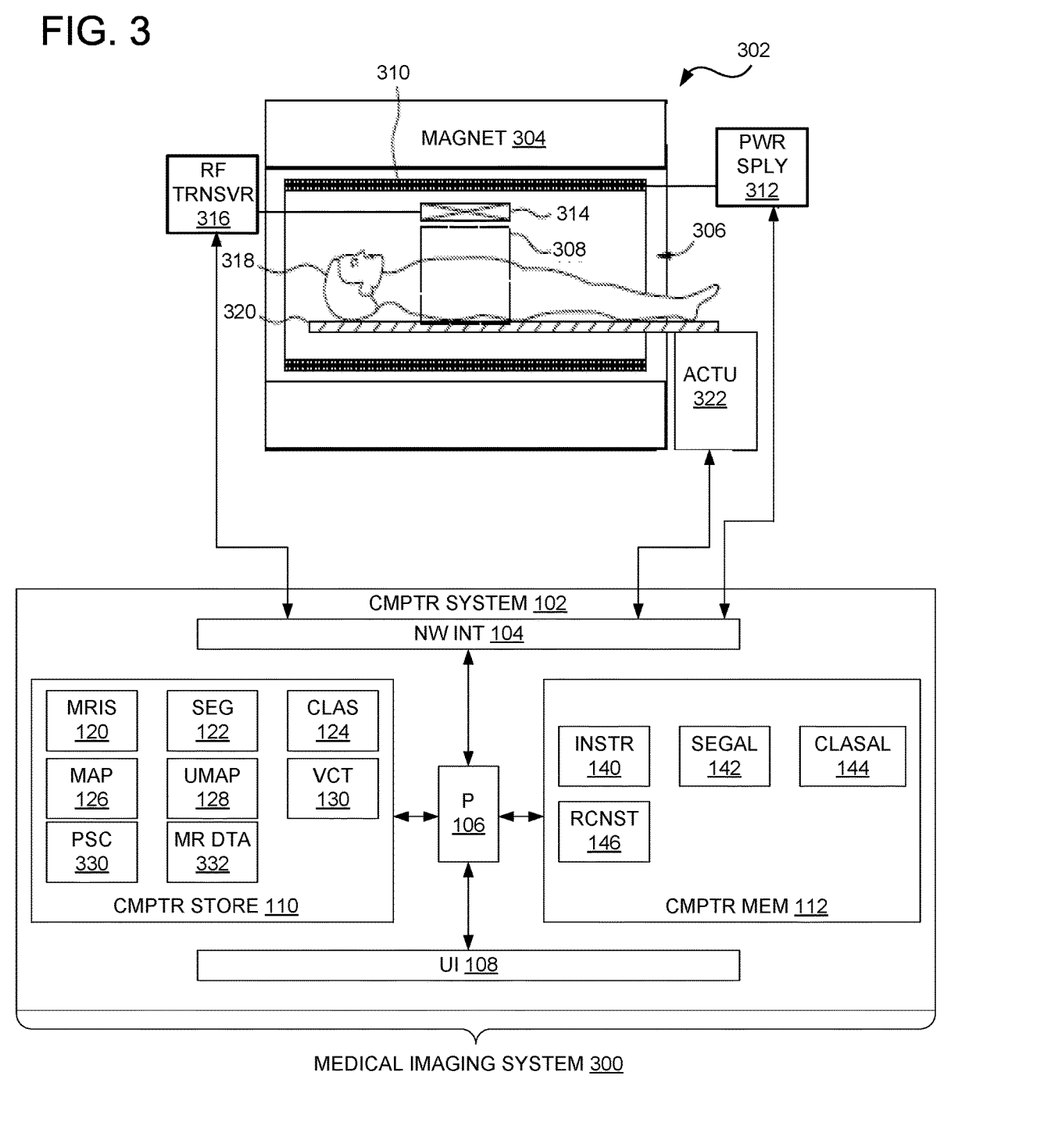
FIG. 3 illustrates a further example of a medical imaging system.

The medical imaging system 300 comprises a magnetic resonance imaging system 302 and a computer system 102 with a processor 106 that is equivalent to the medical imaging system 100 shown in FIG. 1. The magnetic resonance imaging system 102 comprises a magnet 304. The magnet 304 is a superconducting cylindrical type magnet 304 with a bore 306 through it. The use of different types of magnets is also possible; for instance it is also possible to use both a split cylindrical magnet and a so called open magnet. A split cylindrical magnet is similar to a standard cylindrical magnet, except that the cryostat has been split into two sections to allow access to the iso-plane of the magnet, such magnets may for instance be used in conjunction with charged particle beam therapy. An open magnet has two magnet sections, one above the other with a space in-between that is large enough to receive a subject: the arrangement of the two sections area similar to that of a Helmholtz coil. Open magnets are popular, because the subject is less confined. Inside the cryostat of the cylindrical magnet there is a collection of superconducting coils. Within the bore 306 of the cylindrical magnet 304 there is an imaging zone 308 where the magnetic field is strong and uniform enough to perform magnetic resonance imaging.

Within the bore 306 of the magnet there is also a set of magnetic field gradient coils 310 which is used for acquisition of magnetic resonance data to spatially encode magnetic spins within the imaging zone 308 of the magnet 304. The magnetic field gradient coils 310 are connected to a magnetic field gradient coil power supply 312. The magnetic field gradient coils 310 are intended to be representative. Typically magnetic field gradient coils 310 contain three separate sets of coils for spatially encoding in three orthogonal spatial directions. A magnetic field gradient coil power supply 312 supplies current to the magnetic field gradient coils 310. The current supplied to the magnetic field gradient coils 310 is controlled as a function of time and may be ramped or pulsed.

Adjacent to the imaging zone 308 is a radio-frequency coil 314 for manipulating the orientations of magnetic spins within the imaging zone 308 and for receiving radio transmissions from spins also within the imaging zone 308. The radio frequency antenna may contain multiple coil elements. The radio frequency antenna may also be referred to as a channel or antenna. The radio-frequency coil 314 is connected to a radio frequency transceiver 316. The radio-frequency coil 314 and radio frequency transceiver 316 may be replaced by separate transmit and receive coils and a separate transmitter and receiver. It is understood that the radio-frequency coil 314 and the radio frequency transceiver 316 are representative. The radio-frequency coil 314 is intended to also represent a dedicated transmit antenna and a dedicated receive antenna. Likewise the transceiver 316 may also represent a separate transmitter and receivers. The radio-frequency coil 314 may also have multiple receive/transmit elements and the radio frequency transceiver 316 may have multiple receive/transmit channels.

The subject support 320 is attached to an optional actuator 322 that is able to move the subject support and the subject 318 through the imaging zone 308. In this way a larger portion of the subject 318 or the entire subject 318 can be imaged. The transceiver 316, the magnetic field gradient coil power supply 312 and the actuator 322 are all see as being connected to a hardware interface 104 of computer system 102. The computer system 102 is equivalent to the computer system 102 shown in FIG. 1.

The computer storage 110 is further shown as containing pulse sequence commands 330. The computer storage 110 is further shown as containing multiple series of magnetic resonance data 332 that has been acquired when the processor 106 controls the magnetic resonance imaging system 302 with the pulse sequence commands 330. In this example the image reconstruction module 146 reconstructs the magnetic resonance data 332 into the multiple magnetic resonance images 120.

A possible modification to the medical imaging system 300 of FIG. 3 is that the pulse sequence commands cause the magnetic resonance system to acquire the magnetic resonance data according to a magnetic resonance fingerprinting technique. The pulse sequence commands specify a train of pulse sequence repetitions. Each pulse sequence repetition has a pre-defined but varying repetition time. Each pulse sequence repetition comprises either a radio frequency pulse or a sampling event occurring at a pre-defined but varying delay from the start of the pulse sequence repetition, wherein the radio frequency pulse is chosen from a pre-defined but varying distribution of radio frequency pulses. The distribution of radio frequency pulses and timing parameters cause magnetic spins for different tissues to generate specific signal patterns. The pulse sequence commands specify the application of gradient magnetic fields in the at least one direction by controlling the supplied current to the set of gradient coils. For each of the set of magnetic gradient coils the integral of current supplied is a constant for each fixed repetition time.

In this MR fingerprinting example, the computer storage could further be shown as containing magnetic resonance data that was acquired using the pulse sequence commands to control the magnetic resonance imaging system. The computer storage 112 could further be shown as containing a magnetic resonance fingerprinting dictionary. The computer storage could be further shown as containing a magnetic resonance image that was reconstructed using the magnetic resonance data and the magnetic resonance fingerprinting dictionary. The tissue types identified by the magnetic resonance fingerprinting could then be used in the construction of the virtual CT image.

Figure 4:
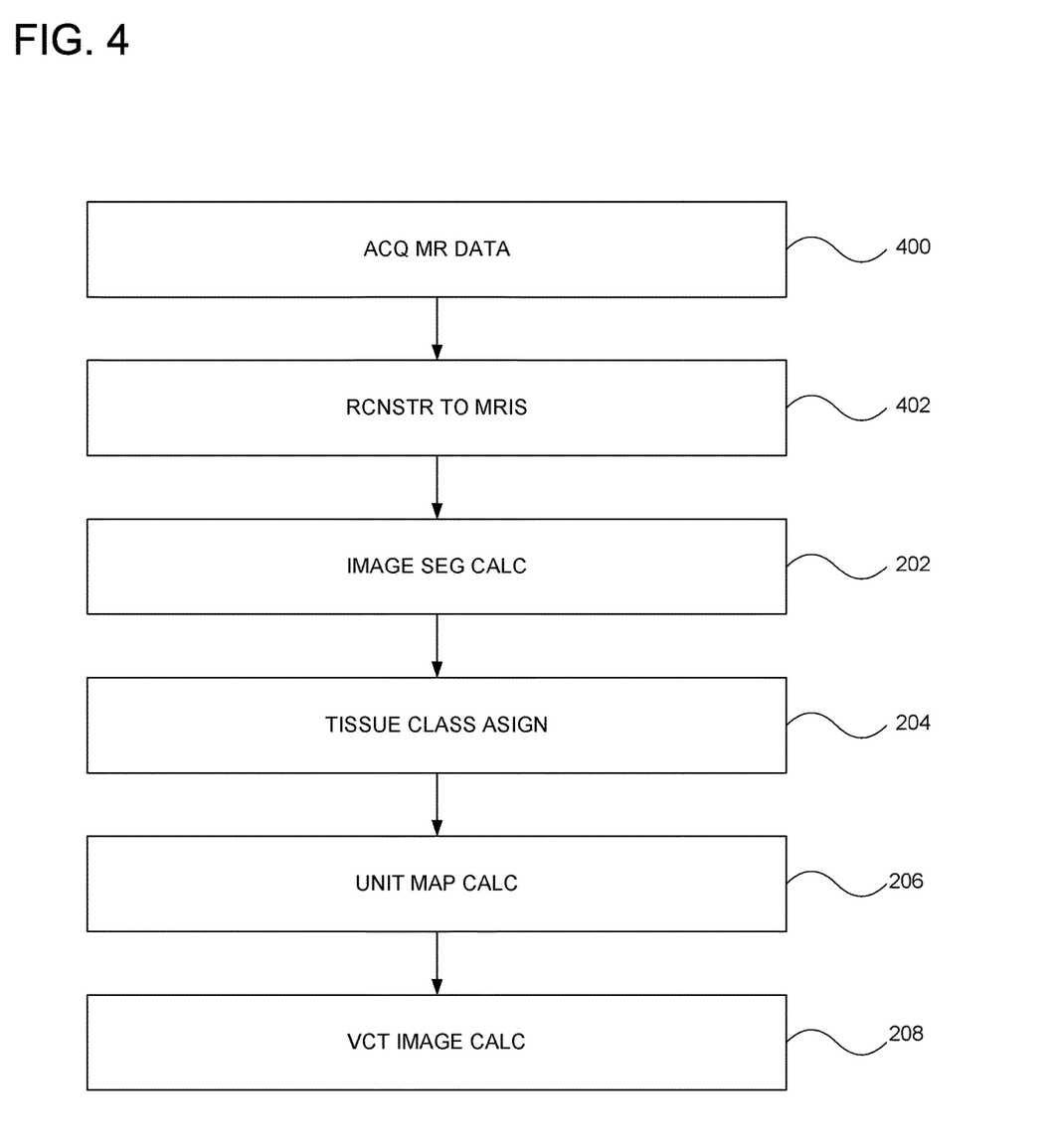
FIG. 4 shows a flow chart that illustrates a method of operating the medical imaging system of FIG. 2.

FIG. 4 shows a flowchart which illustrates a method of operating the medical imaging system 300 of FIG. 3. The method of FIG. 4 is similar to that of FIG. 3 except step number 200 has been replaced with steps 400 and 402. In step 400 the processor controls the magnetic resonance imaging system 302 with the pulse sequence commands 330 to acquire the multiple series of magnetic resonance data 332. Next in step 402 the processor 106 reconstructs the multiple series of magnetic resonance data 332 into the multiple magnetic resonance images 120.

CT is the de facto standard imaging modality due to its high availability and relatively low cost. MRI, however, provides much more advanced diagnostic information due to its multiple contrast generating mechanisms. Wider adoption of MRI in developing countries requires training of radiologists to read the MR images. In practice, many radiologists and referring physicians will need to build their confidence when interpreting MR images, and will rely on CT as the reference. This adds cost and complexity and hampers adoption of MRI. Examples may provide a methods of generating virtual or synthetic CT images which can be made available to radiologists on PACS viewing stations.

Recently methods have been developed to segment and classify MR images in several tissue categories. The purpose of these methods is to provide the information needed for PET attenuation correction without acquiring CT images. A limited set of tissues is classified (like muscle, brain, fat, bone, lung/air) and its representative Hounsfield units are assigned. These methods generally rely on specific additional MR sequences with limited diagnostic value, like 3D ultrashort echo time (UTE) FFE, and have limited resolution.

Alternative methods to classify tissue from MR imaging are emerging, like a dedicated MR acquisition method called Synthetic MRI. It can generate proton density, FLAIR, T1 and T2 images from a single acquisition. An alternative method is called MR Fingerprinting. These methods intend to provide the relevant MR sequence contrasts from a single, relatively short MR sequence.

Examples may provide for a method where classification of tissue types is performed from diagnostic MR images, using one or multiple MR sequences, from which classification the Hounsfield units are assigned to the classified voxels and images are generated to at least the same views as the source MR images. These images are called synthetic or virtual CT image.

The CT images could be stored in a dedicated study and image series, as defined in the DICOM standard. This separate study will represent all relevant patient attributes and display as a CT study. Appropriate billing information for this study will be made available.

Examples might also acquire images after a contrast agent has been administered to a subject. For example the (dynamic) MR contrast agent information from MR series can also be translated into similar image characteristics in the synthetic CT image (time) series.

Alternatively, the synthetic CT images could be generated as part of the process used to generated synthetic MRI images, used for diagnostic purposes. Together with voxel classification in terms of MR parameters (T1, T2, spin density), additional classification is performed to assign the Hounsfield unit, and generate the respective images.

Similarly, when applying MR fingerprinting (MRF), the classification results from the fingerprints are extended by assignment of Hounsfield units. The MRF method can be extended by adding appropriate fingerprint sampling patterns with shorter echo times to improve coverage of e.g. bone structures.

In an additional example, the MR images are co-registered to anatomical atlases, and the Hounsfield assignment can be improved. Also, resolution in the co-registered space can be improved using super-resolution methods.

Figure 5:
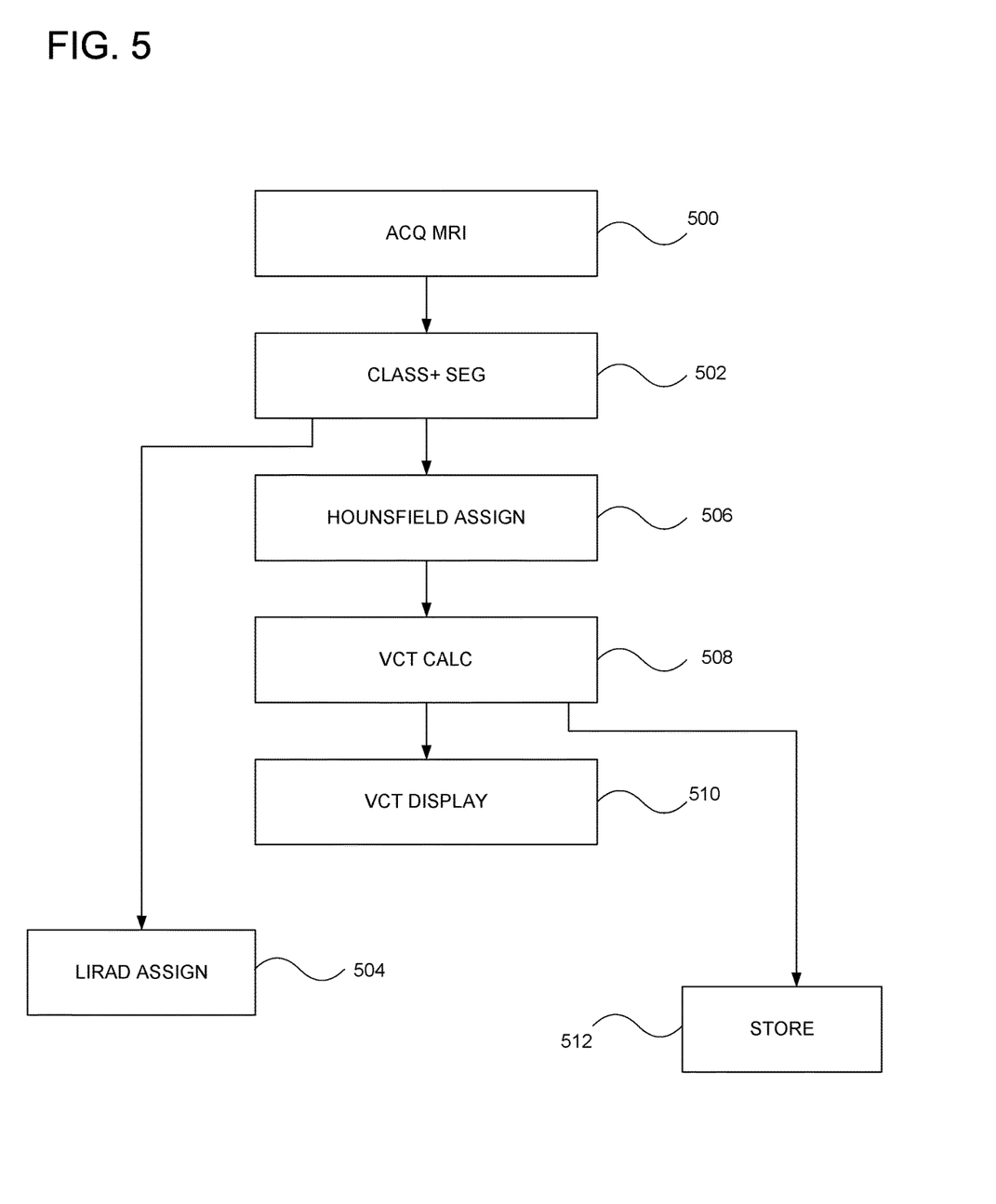
FIG. 5 shows a flow chart that illustrates a further example of a method.

FIG. 5 shows a flowchart which illustrates a further example of a method. First in step 500 MRI images are acquired. This for instance could be performed before and immediately after the administration of an MRI contrast agent to the subject. In this case the images could be considered to be a pre-contrast image and an arterial phase image when the imaging region is the liver. Next the method proceeds to step 502. In step 502 the voxels or pixels are classified and segmented. They are classified to the tissue or pathology type. This for instance may be used for classifying the pixels for the imaged liver using water or fat, classifying them as HCC cells. They may also be classified as cyst cells. In the case where a contrast agent has been administered to a liver the cells may also be classified as normal liver cells, arteries, veins, or even metastasized cells. The magnetic resonance data that is acquired may for instance be acquired to a Dixon magnetic resonance imaging protocol in which case the determination of the water and fat areas is made very easy using this technique. The segmentation and the classification may be used for different purposes. In one use the method proceeds to step 504 and in this the LI-RADS examples are assigned to structures that have been identified in the magnetic resonance images. In another example virtual CT images may be constructed. In this example the method proceeds from step 502 to step 506. In this step Hounsfield units are assigned for the tissue types that were classified in step 502. Once the Hounsfield units have been assigned it is relatively straight forward to calculate a virtual CT image series. This is performed in step 508. The virtual CT image series can then be displayed as is shown in step 510 or may be stored in a database or other storage medium as is performed in step 512. The Hounsfield units 506 for instance may be taken from scientific literature such as papers or from a customized database.

While the invention has been illustrated and described in detail in the drawings and foregoing description, such illustration and description are to be considered illustrative or exemplary and not restrictive; the invention is not limited to the disclosed embodiments.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measured cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

LIST OF REFERENCE NUMERALS 100 medical imaging system
102 computer system
104 hardware interface
106 processor
108 user interface
110 computer storage
112 computer memory
120 multiple magnetic resonance images
122 segmentation of multiple magnetic resonance images
124 tissue classification
126 mapping between tissue classifications and Hounsfield units
128 Hounsfield unit map
130 virtual CT image
140 Machine executable instructions
142 segmentation algorithm
144 magnetic resonance imaging system tissue classifier
146 image processing module
150 display
152 magnetic resonance image
154 virtual CT image
140 pulse sequence commands
142 magnetic resonance data
144 magnetic resonance fingerprinting dictionary
146 magnetic resonance image
150 control module
152 magnetic resonance fingerprint dictionary generating module
154 image reconstruction module
200 receive multiple magnetic resonance images, wherein each of the multiple magnetic resonance images comprises voxels
202 calculate an image segmentation for each of the multiple magnetic resonance images
204 assign a tissue classification to each of the regions using an magnetic resonance imaging tissue classifier
206 calculate a Hounsfield unit map for each of the multiple magnetic resonance images by assigning a Hounsfield unit value to each of the voxels according to the tissue classification
208 calculate a virtual CT image for each of the multiple magnetic resonance images using the Hounsfield unit mapping
300 medical imaging system
302 magnetic resonance imaging system
304 magnet
306 bore of magnet
308 measurement zone or imaging zone
310 magnetic field gradient coils
312 magnetic field gradient coil power supply
314 radio-frequency coil 316 transceiver
318 subject
320 subject support
322 actuator
330 pulse sequence commands
332 multiple series of magnetic resonance data
400 acquire the multiple series of magnetic resonance data by controlling the magnetic resonance imaging system with the pulse sequence commands
402 reconstruct the multiple series of magnetic resonance data into the multiple magnetic resonance images
500 acquire MRI mages
502 segment and classify pixels to tissue/pathology type
504 assign LIRADS example images to classified structures
506 assign Hounsfield units to pixels
508 create virtual ct images
510 display virtual CT images
512 store as DICOM CT image objects

The invention claimed is:

1. A magnetic resonance imaging system comprising:
   a memory for storing machine executable instructions; and
   a processor for controlling the magnetic resonance imaging system, wherein execution of the machine executable instructions causes the processor to:
   acquire multiple series of magnetic resonance data of respective different contrast types, from a subject and acquired by several acquisition protocols;
   reconstruct the multiple series of magnetic resonance data into the multiple magnetic resonance images, wherein each of the multiple magnetic resonance images comprises voxels;
   calculate an image segmentation for each of the multiple magnetic resonance images, wherein the image segmentation divides each of the multiple magnetic resonance images into regions;
   assign a tissue classification to each of the regions using a magnetic resonance imaging tissue classifier;
   calculate a Hounsfield unit map for the magnetic resonance image by assigning a Hounsfield unit value to each of the voxels according to the tissue classification, wherein the Hounsfield mapping comprises a mapping between the tissue classification to Hounsfield units; and
   calculate a virtual Computed Tomography (CT) image for each of the multiple magnetic resonance images using the Hounsfield unit mapping.

2. The magnetic resonance imaging system of claim 1, wherein execution of the machine executable instructions further causes the processor to provide the virtual CT image on a display.

3. A medical imaging method, wherein the method comprises:
   accessing multiple magnetic resonance images of respective different contrast types and reconstructed from multiple series of magnetic resonance data, from a subject and acquired by several acquisition protocols, wherein each of the multiple magnetic resonance images comprises voxels;
   calculating an image segmentation for each of the multiple magnetic resonance images, wherein the image segmentation divides each of the multiple magnetic resonance images into regions;
   assigning a tissue classification to each of the regions;
   calculating a Hounsfield unit map for each of the multiple magnetic resonance images by assigning a Hounsfield unit value to each of the voxels according to the tissue classification, wherein the Hounsfield mapping comprises a mapping between the tissue classification to Hounsfield units; and
   calculating a virtual Computed Tomography (CT) image for each of the multiple magnetic resonance images using the Hounsfield unit mapping.

4. The method of claim 3, further comprising providing the virtual CT image on a display.

5. A computer program product comprising machine executable instructions for execution by a processor controlling a medical imaging system, wherein execution of the machine executable instructions causes the processor to:
   access multiple magnetic resonance images of respective different contrast types and reconstructed from multiple series of magnetic resonance data, from a subject and acquired by several acquisition protocols, wherein each of the multiple magnetic resonance images comprises voxels;
   calculate an image segmentation for each of the multiple magnetic resonance images, wherein the image segmentation divides each of the multiple magnetic resonance images into regions;
   assign a tissue classification to each of the regions using a magnetic resonance imaging tissue classifier;
   calculate a Hounsfield unit map for each of the multiple magnetic resonance images by assigning a Hounsfield unit value to each of the voxels according to the tissue classification, wherein the Hounsfield mapping comprises a mapping between the tissue classification to Hounsfield units; and
   calculate a virtual Computed Tomography (CT) image for each of the multiple magnetic resonance images using the Hounsfield unit mapping.

6. The computer program product of claim 5, wherein execution of the machine executable instructions further causes the processor to provide the virtual CT image on a display.

7. A medical imaging system comprising:
   a memory for storing machine executable instructions; and
   a processor for controlling the medical system, wherein execution of the machine executable instructions causes the processor to:
   access multiple magnetic resonance images of respective different contrast types and reconstructed from multiple series of magnetic resonance data, from a subject and acquired by several acquisition protocols, wherein each of the multiple magnetic resonance images comprises voxels;
   calculate an image segmentation for each of the multiple magnetic resonance images, wherein the image segmentation divides each of the multiple magnetic resonance images into regions;
   assign a tissue classification to each of the regions using a magnetic resonance imaging tissue classifier;
   calculate a Hounsfield unit map for each of the multiple magnetic resonance images by assigning a Hounsfield unit value to each of the voxels according to the tissue classification, wherein the Hounsfield mapping comprises a mapping between the tissue classification to Hounsfield units; and
   calculate a virtual Computed Tomography (CT) image for each of the multiple magnetic resonance images using the Hounsfield unit mapping, wherein the medical system further comprises a magnetic resonance imaging system for acquiring the multiple series of magnetic resonance data from a subject, wherein the memory further stores pulse sequence commands, said pulse sequence commands cause the processor to acquire magnetic resonance data by varying any one of the following: a flip angle, Time to Echo (TE), Repetition Time (TR), or combinations thereof in the form of a MR fingerprinting magnetic resonance imaging protocol that causes the data to be acquired using a predetermined but pseudo random variation of the one or combination of flip angle, TE, or TR, wherein execution of the machine executable instructions further causes the processor to:

acquire the multiple series of magnetic resonance data by controlling the magnetic resonance imaging system with the pulse sequence commands.

8. The medical imaging system of claim 7, wherein the pulse sequence commands cause the magnetic resonance imaging system to acquire the multiple series of magnetic resonance data according to an arterial spin labeling magnetic resonance imaging protocol.

9. The medical system of claim 7, wherein the medical imaging system further comprises a display, wherein execution of the machine executable instructions further causes the processor to display the virtual CT image for each of the multiple magnetic resonance images.

10. The medical system of claim 9, wherein the virtual CT image is displayed next to a corresponding image, wherein the corresponding image is selected from the multiple magnetic resonance images.

11. The medical system of claim 7, wherein the tissue classification is according to a finite number of tissue types that comprise any one of the following: water, fat, Hepatocellular carcinoma cells, carcinoma cells, cyst cells, arteries, veins, Metastasis cells, bone tissue, blood, epithelial cells, muscle tissue, interstitial cells, nerve tissue, connective tissue, cartilage, and combinations thereof.

12. The medical system of claim 7, wherein the multiple magnetic resonance images comprise at least: a pre-contrast image or a late post contrast image, an arterial phase image, a post venous phase image, and a late enhancement image.

13. The medical system of claim 7, wherein the magnetic resonance imaging tissue classifier assigns the tissue classification to each of the regions at least partially using an anatomical model.

14. The medical system of claim 7, wherein the magnetic resonance imaging tissue classifier assigns the tissue classification to each of the regions at least partially by:

computing a representative voxel value for each of the regions;

normalizing the representative voxel value for each of the regions;

assigning the tissue classification to each of the regions by matching the normalized representative voxel with a predetermined range for the tissue classification.

15. The medical system of claim 7, wherein execution of the machine executable instructions further causes the processor to assign Liver Imaging Reporting and Data System (LIRADS) example images to identified tissues types in the virtual CT image for each of the multiple magnetic resonance images.

16. The medical system of claim 7, wherein the virtual CT image for each of the multiple magnetic resonance images is stored in an image database.

* * * * *